United States Patent
Grandner et al.

(10) Patent No.: US 11,957,480 B2
(45) Date of Patent: *Apr. 16, 2024

(54) SYSTEMS AND METHODS FOR SLEEP OPTIMIZATION

(71) Applicants: Arizona Board of Regents on Behalf of the University of Arizona, Tucson, AZ (US); The Trustees of the University of Pennsylvania, Philadelphia, PA (US)

(72) Inventors: Michael Grandner, Tucson, AZ (US); Michael Perlis, Philadelphia, PA (US)

(73) Assignees: Arizona Board of Regents on Behalf of the University of Arizona, Tucson, AZ (US); The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/860,520

(22) Filed: Jul. 8, 2022

(65) Prior Publication Data
US 2022/0338799 A1 Oct. 27, 2022

Related U.S. Application Data

(63) Continuation of application No. 16/834,990, filed on Mar. 30, 2020, now Pat. No. 11,382,560.

(60) Provisional application No. 62/825,642, filed on Mar. 28, 2019.

(51) Int. Cl.
*A61B 5/00* (2006.01)
*G16H 10/60* (2018.01)
*G16H 20/30* (2018.01)
*G16H 20/70* (2018.01)
*G16H 50/30* (2018.01)

(52) U.S. Cl.
CPC .......... *A61B 5/4809* (2013.01); *A61B 5/0002* (2013.01); *A61B 5/4812* (2013.01); *G16H 10/60* (2018.01); *G16H 20/30* (2018.01); *G16H 20/70* (2018.01); *G16H 50/30* (2018.01)

(58) Field of Classification Search
CPC ... A61B 5/4809; A61B 5/0002; A61B 5/4812; G16H 20/30; G16H 10/60; G16H 50/30; G16H 20/70
USPC ........................................................ 340/575
See application file for complete search history.

(56) References Cited

U.S. PATENT DOCUMENTS

| | | | |
|---|---|---|---|
| 10,206,618 B2 * | 2/2019 | Vuong | G16H 40/67 |
| 10,207,075 B1 * | 2/2019 | Kahn | A61M 21/02 |
| 10,376,207 B2 * | 8/2019 | Aubert | G16H 50/50 |

(Continued)

*Primary Examiner* — Zhen Y Wu
(74) *Attorney, Agent, or Firm* — Blank Rome LLP (57) ABSTRACT

Computer-implemented systems and methods for sleep optimization are disclosed. In certain embodiments, the system includes one or more peripheral devices, a network, one or more networked computers, and one or more remote servers. The peripheral devices and/or the networked computers collect one or more types of sleep data, calculate one or more sleep parameters, and transmit said sleep parameters to the one or more remote servers. The remote servers then perform calculations to determine optimal sleep recommendations. The sleep recommendations are then output to one or more networked computers and/or one or more peripheral devices as adjustments to sleep time and sleep duration.

20 Claims, 7 Drawing Sheets

(56) References Cited

U.S. PATENT DOCUMENTS

| | | | | |
|---|---|---|---|---|
| 10,532,183 B2* | 1/2020 | Raut | .................... | A61B 5/4815 |
| 10,568,565 B1* | 2/2020 | Kahn | .................... | A61B 5/1126 |
| 10,799,175 B2* | 10/2020 | Rangan | ................ | A61B 5/4806 |
| 2011/0015495 A1* | 1/2011 | Dothie | ................. | A47C 31/123 |
| | | | | 600/300 |
| 2011/0267196 A1* | 11/2011 | Hu | ....................... | A61B 5/4815 |
| | | | | 340/575 |
| 2011/0295083 A1* | 12/2011 | Doelling | ................. | A61B 5/11 |
| | | | | 600/407 |
| 2012/0238800 A1* | 9/2012 | Naujokat | ............... | A61B 5/318 |
| | | | | 600/26 |
| 2016/0045035 A1* | 2/2016 | Van Erlach | .......... | A61B 5/0036 |
| | | | | 700/279 |
| 2016/0073951 A1* | 3/2016 | Kahn | ................... | A61B 5/7275 |
| | | | | 600/595 |
| 2016/0151603 A1* | 6/2016 | Shouldice | .............. | G16H 20/30 |
| | | | | 600/26 |
| 2017/0095670 A1* | 4/2017 | Ghaffari | ............. | A61N 1/36139 |
| 2017/0312477 A1* | 11/2017 | Hashizaki | ............ | A61B 5/4815 |
| 2017/0347949 A1* | 12/2017 | Arnold | ................. | A61B 5/7405 |
| 2018/0027988 A1* | 2/2018 | Poodeh | ................. | A47G 9/1027 |
| 2018/0085050 A1 | 3/2018 | Grandner et al. | | |
| 2018/0229040 A1* | 8/2018 | Srivastava | ......... | A61N 1/36071 |
| 2018/0261310 A1* | 9/2018 | Edwards | ................ | G16H 50/20 |
| 2018/0264224 A1* | 9/2018 | Gronfier | .............. | A61B 5/6898 |
| 2018/0368756 A1* | 12/2018 | Amin | .................... | G16H 40/67 |
| 2018/0368757 A1* | 12/2018 | Amin | .................... | G16H 40/67 |
| 2019/0070386 A1* | 3/2019 | Raut | ....................... | A61B 5/375 |
| 2019/0124032 A1* | 4/2019 | Ganesh | .................. | G06F 1/163 |
| 2019/0183415 A1* | 6/2019 | Rytky | .................. | A61B 5/4806 |
| 2020/0060543 A1* | 2/2020 | Federoff | ................ | G16H 50/70 |
| 2020/0138365 A1* | 5/2020 | Lack | ..................... | A61B 5/4836 |
| 2020/0146619 A1* | 5/2020 | Molina | .................. | A61B 5/742 |
| 2020/0368488 A1* | 11/2020 | Sato | ...................... | G04G 13/025 |
| 2020/0397367 A1* | 12/2020 | Kinnunen | ............ | A61B 5/6801 |

* cited by examiner

SYSTEMS AND METHODS FOR SLEEP OPTIMIZATION

CROSS-REFERENCE TO RELATED APPLICATIONS

This is a continuation of U.S. patent application Ser. No. 16/834,990, filed Mar. 30, 2020, which claims the benefit of U.S. Provisional Application No. 62/825,642, filed Mar. 28, 2019, the entire contents of which are hereby incorporated by reference.

FIELD OF THE INVENTION

The present invention relates to computer-implemented systems and methods for optimizing and/or calibrating sleep over a period of time using a consolidated technological platform.

BACKGROUND OF THE INVENTION

Recent CDC data estimate that over ⅓ of US adults do not get the recommended amount of sleep to maintain optimal health and functioning. (These estimates are consistent with those from other industrialized nations as well.) This is alarming, since insufficient sleep is associated with weight gain and obesity, cardiovascular disease, diabetes, inflammation, pain, cancer, fatigue, accidents and injuries, and other adverse outcomes. This has been identified as a major unmet public health problem by the federal government, with a goal of increasing the number of adults who achieve adequate sleep identified as a national health priority in "Healthy People 2020." However, no strategy currently exists to meet this goal. There are several barriers to achieving this. First, simply making recommendations does not change behavior. For example, telling people to quit smoking, reduce drinking, get more exercise, or reduce dietary intake is not effective in changing behavior for most people. Strategies for effective behavior change need to be developed. Second, sleep needs are difficult to quantify. Some people may need more or less sleep, and these universal recommendations do not address this. Third, ability to sleep also varies substantially from person to person, and more than this, individual sleep need substantially varies over time in relation to age, health, and performance demands. Any successful method for prescribing optimal sleep duration must be based on "the idiographic and not the nomothetic" (i.e., sleep duration must be assessed and optimized on an individual basis).

There has been a proliferation of devices that measure sleep and display sleep data, but such devices and systems do not provide science-based, data driven, guidance about how to get more sleep and/or what amount of sleep (and its timing) is optimal for a given individual. Existing "sleep coaching" is limited because: (1) recommendations are not individually-tailored; (2) recommendations are not actionable; (3) recommendations are not feasible; (4) recommendations are not self-correcting; and (5) recommendations are just tips/suggestions.

Consequently, there is a need for systems and methods for optimizing and/or calibrating sleep time over a period of time using a consolidated technological platform.

SUMMARY OF THE INVENTION

It is therefore an object of the exemplary embodiments disclosed herein to address the disadvantages in the art and provide a sleep optimization system that uses networked peripheral devices to aggregate scientific data, quantifies various behavioral and physical characteristics, thereby analyzing and quantifying sleep times and/or patterns.

It is another object of the invention to have a sleep optimization system that utilizes the analyzed data to provide recommendations that are individually-tailored, actionable, feasible, and self-correcting.

It is another object of the invention to provide integration of one's sleep data from multiple sources on one platform.

It is another object of the invention to provide a program that uses algorithms to provide individualized and self-correcting recommendations.

It is yet another object of the invention to provide recommendations that are focused on sleep timing, duration, and daytime function, thereby optimizing sleep.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF PREFERRED EMBODIMENTS

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in a similar manner to accomplish a similar purpose. Several preferred embodiments of the invention are described for illustrative purposes, it being understood that the invention may be embodied in other forms not specifically shown in the drawings.

Sleep and circadian rhythms are a key component of health and well-being in mammals. The absence of sleep can have negative effects on physical, mental, and emotional health. Too little or too much sleep can have a significant impact on cognition, cardiovascular health, the immune system, and overall health. Consequently, monitoring and regulating sleep patterns and/or timing is important in improving the general health of individuals.

Figure 1:
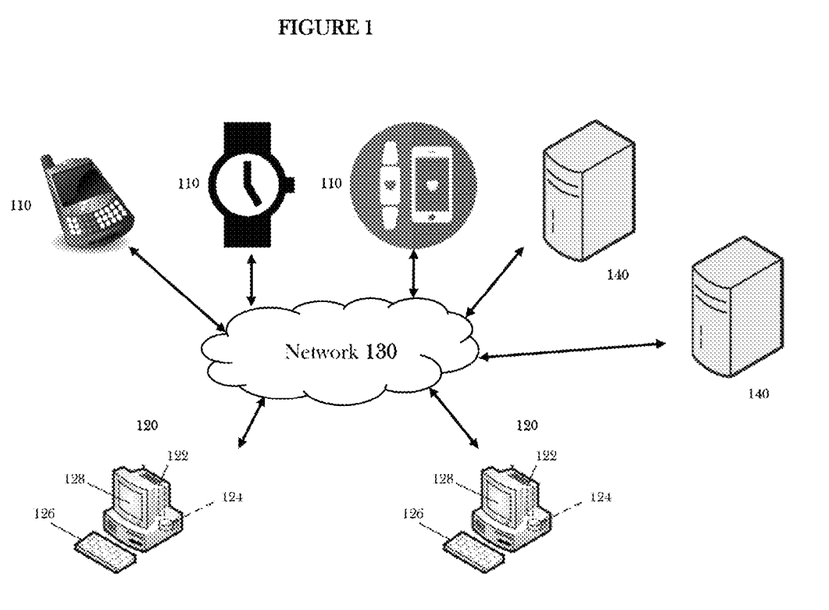
FIG. 1 is an exemplary embodiment of the sleep optimization system.

FIG. 1 is an exemplary embodiment of the sleep optimization system. In the exemplary system 100, one or more peripheral devices 110 are connected to one or more computers 120 through a network 130. Examples of peripheral devices 110 include clocks, smartphones, smart-clocks, tablets, thermometers, wearable devices such as smartwatches or EEGs, medical devices such as EKGs and blood pressure monitors, glucose monitors, sensors (physiological or otherwise), servers with databases that contain a user's personal data, and any other devices that collect data that can be used as sleep data are known in the art. The network 130 may be a wide-area network, like the Internet, or a local area network, like an intranet. Because of the network 130, the physical location of the peripheral devices 110 and the computers 120 has no effect on the functionality of the hardware and software of the invention. Both implementations are described herein, and unless specified, it is contemplated that the peripheral devices 110 and the computers 120 may be in the same or in different physical locations. Communication between the hardware of the system may be accomplished in numerous known ways, for example using network connectivity components such as a modem or Ethernet adapter. The peripheral devices 110 and the computers 120 will both include or be attached to communication equipment. Communications are contemplated as occurring through industry-standard protocols such as HTTP.

Each computer 120 is comprised of a central processing unit 122, a storage medium 124, a user-input device 126, and a display 128. Examples of computers that may be used are: commercially available personal computers, open source computing devices (e.g. Raspberry Pi), commercially available servers, and commercially available portable device (e.g. smartphones, smartwatches, tablets). In one embodiment, each of the peripheral devices 110 and each of the computers 120 of the system may have the sleep optimization software related to the system installed on it. In such an embodiment, sleep data may be stored locally on the networked computers 120 or alternately, on one or more remote servers 140 that are accessible to any of the networked computers 120 through a network 130. In alternate embodiments, the sleep optimization software runs as an application on the peripheral devices 110.

Figure 2:
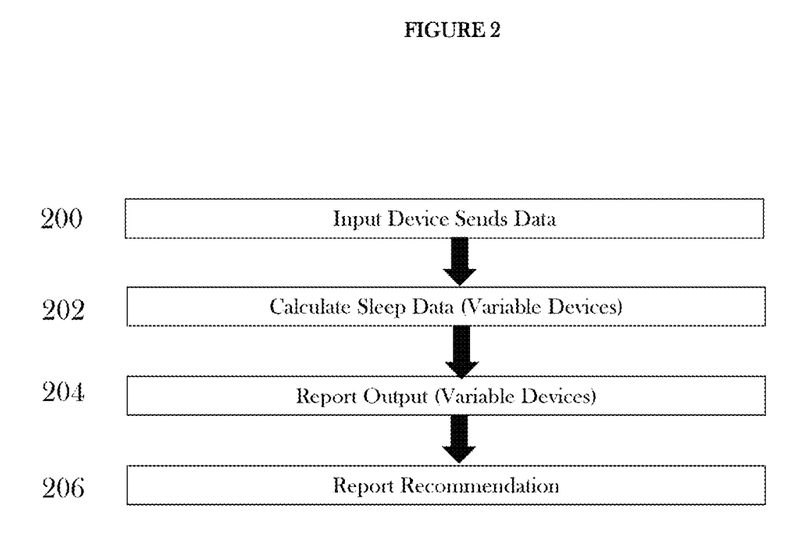
FIG. 2 is an exemplary logic flow diagram demonstrating how the sleep optimization system aggregates, analyzes, and quantifies sleep data in order to output recommendations to a user.

FIG. 2 is an exemplary logic flow diagram of the software processes performed using the hardware described in FIG. 1 above.

Goals of the present invention include determining the individual's best fit sleep duration and phase for optimal outcomes (e.g., daytime performance, mood, etc.) In general, the methods of the present invention involve collecting information about an individual's sleep duration and phase (naturally occurring or systematically manipulated up and downward titration across multiple sleep period phases) while concurrently gathering data on outcomes of interest ("benchmarks"). These represent the variables that are of interest to the individual, around which they wish to modify their sleep. This can be one or more variables; although there is no upper limit, it is recommended that there should be no more than 5 benchmarks.

These benchmarks can consist of any quantifiable outcome that is of interest to a person. It can include physiologic data collected by some sort of device (e.g., blood pressure, blood glucose, heart rate, brain waves, breathing rate), behavioral data collected by some sort of device (e.g., movement, eating behavior, use of devices), environmental data collected by some sort of device (e.g., temperature, light levels), subjective data collected by an input device (e.g., rating scales, written input, audio input), existing data about an individual from an external source (e.g., medical record, school record), or some other external data.

The benchmarks used to input into the algorithm can be limited to a certain number, and can be specifically chosen by an individual. For example, an individual can choose that the benchmarks of value to them are mood (self-rating), blood pressure (biological measure), and focus (measured using an app). All three of these different measurements will be obtained at various intervals from various sources and will then be fed into the sleep optimization program.

The sleep continuity data used to calibrate sleep can be based on passive or active measures (e.g., actigraphy or sleep diary based measures). In general, the sleep diary data will work better (than e.g., actigraphy) for performance measures (self-report and down the road biologic measures like blood pressure, ALC, etc.).

Figure 3A:
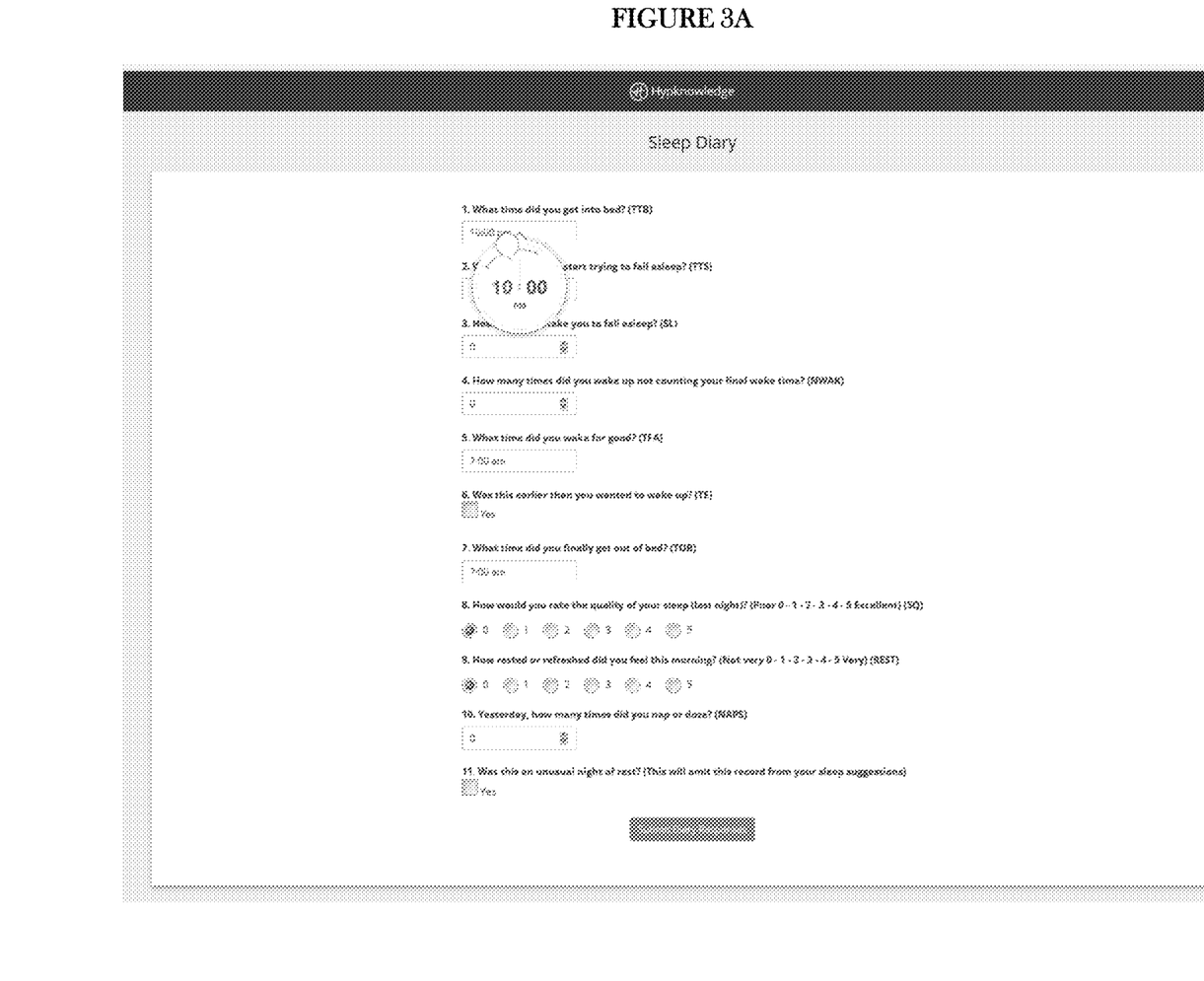
FIG. 3A is a screenshot of the graphical user interface in which the sleep optimization system displays an online sleep diary.
Figure 3B:
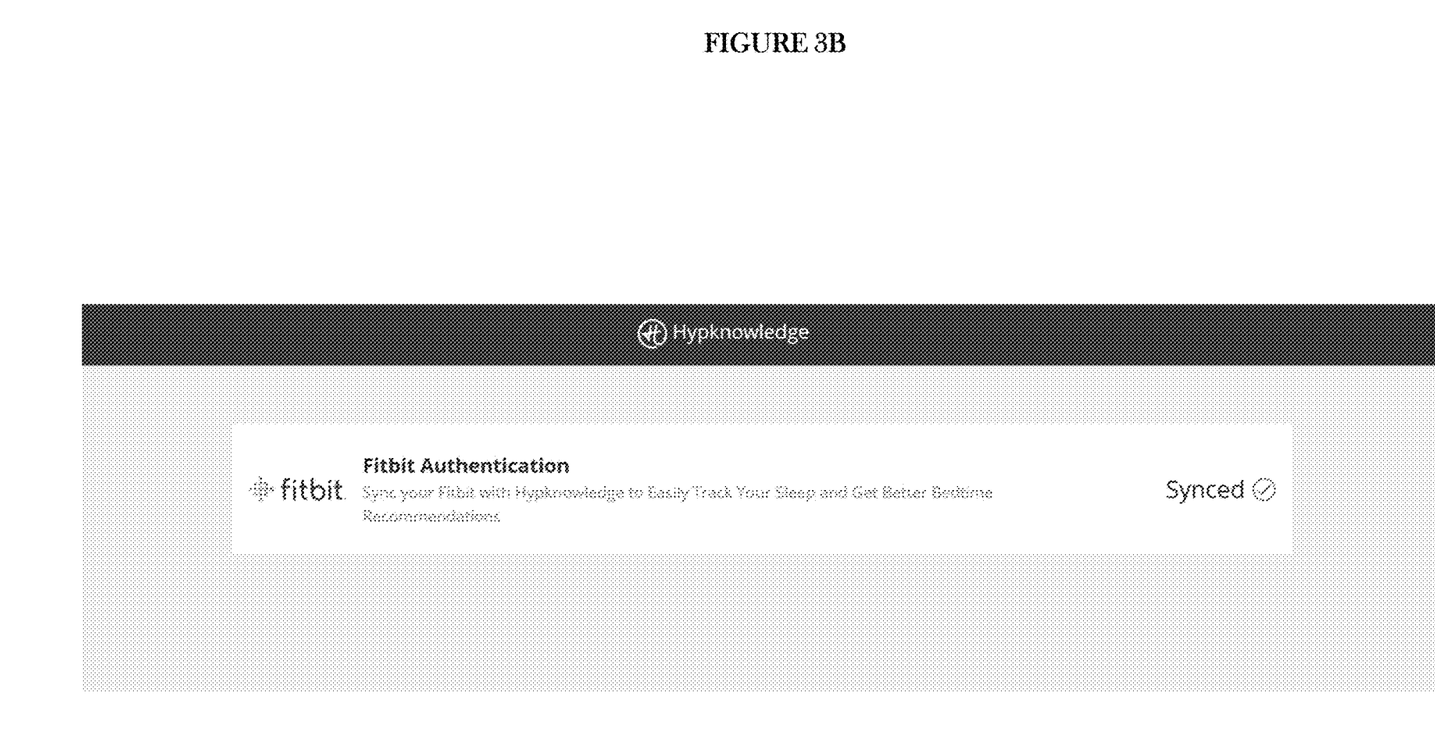
FIG. 3B is a screenshot of the graphical user interface in which data capture from a peripheral device is confirmed.

In certain implementations of the invention, Likert scales may be used to obtain data. The logic flow, in accordance with an exemplary embodiment of the invention commences at step 200, "Input Device Sends Data" where an input device receives data such as time spent in bed and sleep time. The input device may be a peripheral device 110 and/or a user-input device 126 in any combination. Step 200 includes gathering benchmark data (DVs) from peripheral devices, databases, and/or user input. In certain embodiments, the software of the present invention may require the user to maintain a sleep diary, as shown in FIG. 3A. That sleep diary may collect such data as the time a user got into bed, how long it took to fall asleep, how many times the user woke up during sleep, what time the user woke up for good, that time the user got out of bed, and how many times the user took a nap. Other factors considered in certain implementations of the invention may be subjective, such as quality of sleep and how refreshed the user felt in the morning. Another example of data collection from a peripheral device, a FitBit®, is shown in FIG. 3B. Benchmark data related to the user may also be collected. That benchmark data assists the system in creating a baseline for the user against which sleep optimization is performed. Other sleep data may be collected as well, as described in U.S. Pat. Pub. No. US 2018/0085050 A1, the entirety of which is incorporated herein by reference.

At step 202, "Calculate Sleep Data (Variable Devices)," the sleep optimization system calculates sleep parameters. The data is manipulated in a number of ways by the software of the present invention. For example, the data may be used to 1) create a duration by phase data table where each cell contains the average DV values; 2) create data plots duration by phase for each DV; 3) determine which duration by phase sleep profile is associated with the most optimal performance for each DV; and 4) determine which duration by phase sleep profile is associated with optimal performance for all the DVs (best fit) with weighted (ordered) DVs.

Figure 3C:
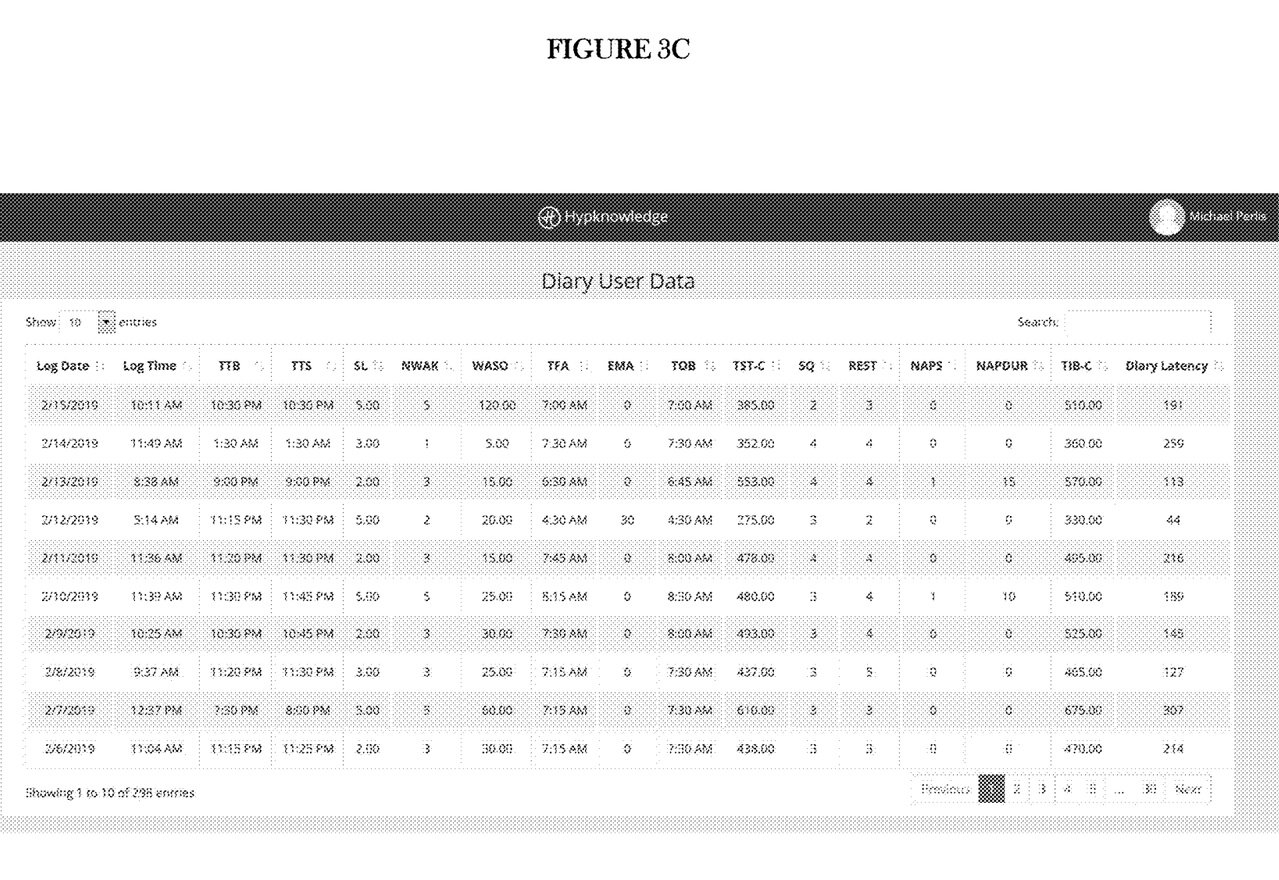
FIG. 3C is a screenshot of the graphical user interface in which user data associated with the online sleep diary is displayed.
Figure 3D:
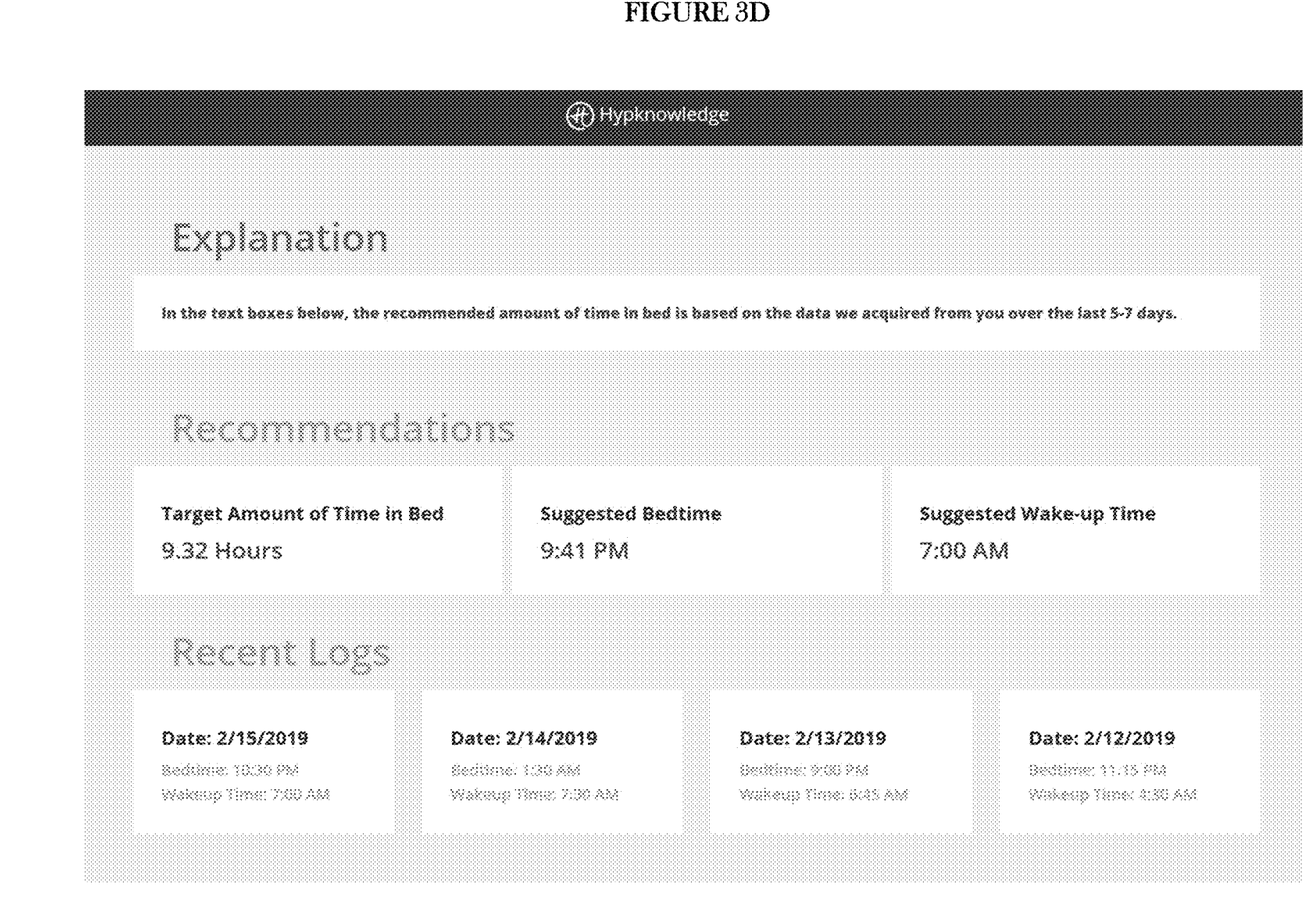
FIG. 3D is a screenshot of the graphical user interface in which user recommendations are shown on a dashboard.

At step 204, "Report Output (Variable Devices)," the sleep optimization system outputs a report summarizing the While all data designated above will be available to the user, a simple recommendation will be provided online (site user dashboard), via email or texts, and possible via verbal interfaces such as Amazon's Alexa. An exemplary breakdown of sleep diary data across a number of dates is shown in FIG. 3C. An exemplary dashboard providing recommendations is shown in FIG. 3D.

As shown in FIG. 3C, "time to bed" (TTB) represents the time that the person got into bed. Another parameter includes "time to sleep" (TTS), the time spent trying to fall asleep, and "time out of bed" (TOB). Another parameter, "total time asleep" (TST) can be estimated by any means, including self-reporting in a diary, estimated by movement patterns, or estimated by other biometric signals such as heart rate or brain signals. The other parameters include "sleep latency, or latency to fall asleep" (SL), which is measured in seconds, minutes, or hours, "time awake after initial sleep onset" (WASO), and "time spent in bed awake after the final awakening, or early morning awakenings" (EMA). "Total sleep time" would ideally be calculated by taking time in bed and subtracting these three parameters (i.e., TST=TTB−SL−WASO−EMA). Other parameters include "number of suspected awakenings" (NWAK). Other sleep parameters shown include an indication of "sleep quality" (SQ), an indication of how refreshed the person felt in the morning (REST), an indication of the number of naps taken (NAPS), and the duration of the naps (NAPDUR).

Figure 3E:
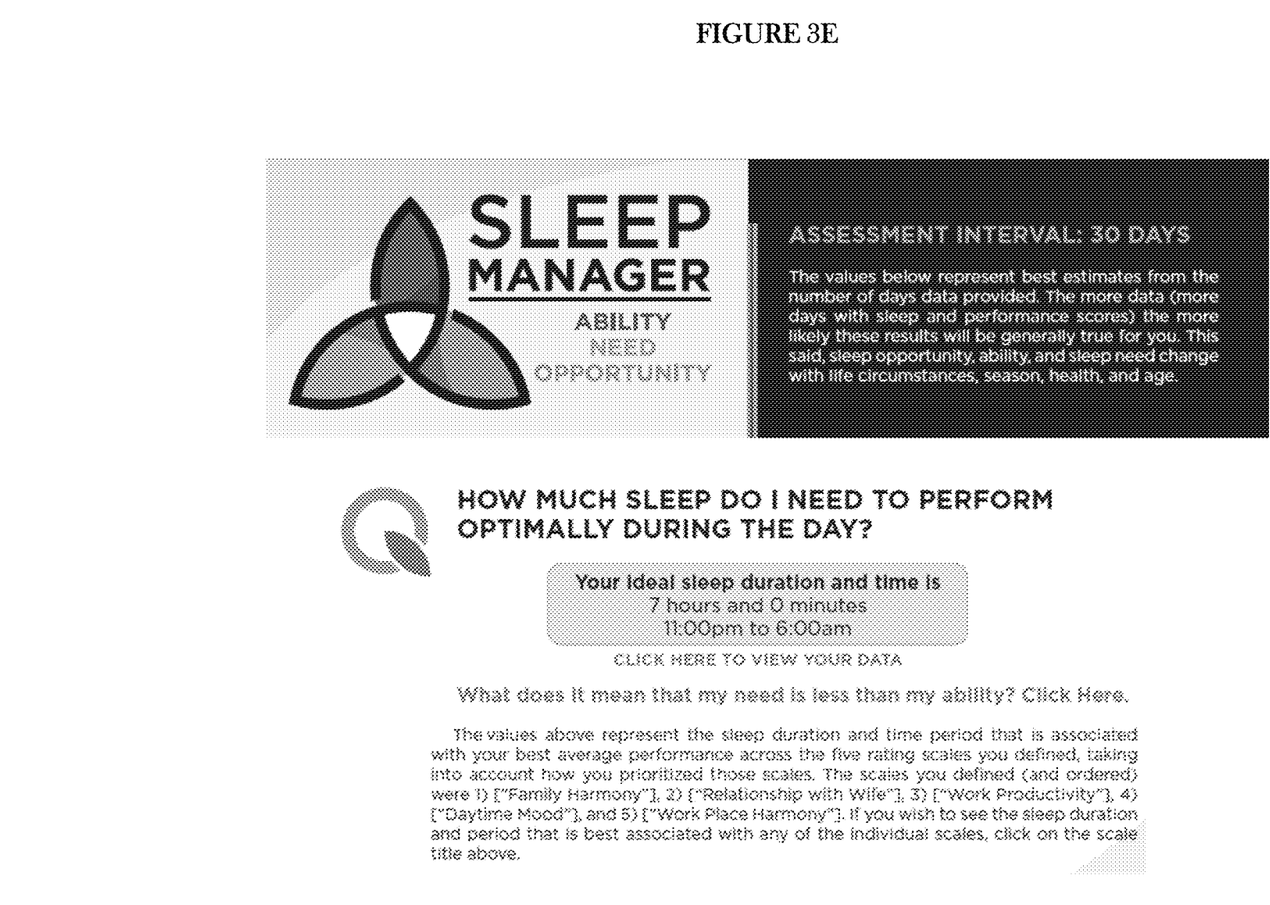
FIG. 3E is a screenshot of the graphical user interface in which an optimized sleep recommendation is output to the user.

At step 206, "Report Recommendation," the sleep optimization system consolidates all of the collected and analyzed data discussed in steps 200-204 to arrive at a sleep duration and sleep time recommendation for the user. Other recommendation may include optimal environmental conditions such as ambient temperature. FIG. 3E is an exemplary interface showing that ideal sleep duration and sleep time recommendation for a typical user. In certain embodiments, recommendations provided to the user are recommendations for modifying the user's benchmark data.

The foregoing description and drawings should be considered as illustrative only of the principles of the invention. The invention is not intended to be limited by the preferred embodiment and may be implemented in a variety of ways that will be clear to one of ordinary skill in the art. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A sleep optimization system comprising a server, wherein the server:
   receives one or more types of sleep data comprising a plurality of sleep parameters from one or more peripheral devices or computers, wherein the sleep parameters are uniquely tailored to an individual;
   calculates from the plurality of sleep parameters a duration by phase data table where each cell contains the average benchmark data values (DVs);
   calculates data plots duration by phase for each DV;
   determines which duration by phase sleep profile is associated with most optimal performance for each DV; and
   determines which duration by phase sleep profile is associated with optimal performance for all of the DVs with weighted DVs to output optimal sleep recommendations as adjustments to sleep time and sleep duration;
   wherein the optimal sleep recommendations are calculated using an indication of "time to bed" (TOB), "time to sleep" (TTS), or "time out of bed" (TOB).

2. The system of claim 1, wherein the one or more peripheral devices comprise one or more clocks, smartphones, smart-clocks, tablets, thermometers, smartwatches, EEGs, EKGs, blood pressure monitors, glucose monitors, or physiological sensors.

3. The system of claim 1, wherein the one or more computers comprise networked computers storing physiological data.

4. The system of claim 1, wherein the DVs comprise physiologic data, environmental data, subjective data collected by an input device, and existing data about the individual from an external data source.

5. The system of claim 4, wherein the subjective data is one or more of mood or focus.

6. The system of claim 1, wherein the sleep recommendations are output via an online dashboard, via email or texts, or via verbal interfaces.

7. The system of claim 1, wherein the server further outputs optimal environmental conditions for sleep.

8. The system of claim 1, wherein the sleep data is collected using a Likert scale.

9. The system of claim 1, wherein the sleep parameters comprise sleep continuity data.

10. The system of claim 1, wherein the DVs are measured at predetermined intervals.

11. A sleep optimization method comprising:
    receiving one or more types of sleep data comprising a plurality of sleep parameters from one or more peripheral devices or computers, wherein the sleep parameters are uniquely tailored to an individual;
    calculating from the plurality of sleep parameters a duration by phase data table where each cell contains the average benchmark data values (DVs);
    calculating data plots duration by phase for each DV;
    determining which duration by phase sleep profile is associated with most optimal performance for each DV; and
    determining which duration by phase sleep profile is associated with optimal performance for all of the DVs with weighted DVs to output optimal sleep recommendations as adjustments to sleep time and sleep duration;
    wherein the optimal sleep recommendations are calculated using an indication of "time to bed" (TOB), "time to sleep" (TTS), or "time out of bed" (TOB).

12. The method of claim 11, wherein the one or more peripheral devices comprise one or more clocks, smartphones, smart-clocks, tablets, thermometers, smartwatches, EEGs, EKGs, blood pressure monitors, glucose monitors, or physiological sensors.

13. The method of claim 11, wherein the one or more computers comprise networked computers storing physiological data.

14. The method of claim 11, wherein the DVs comprise physiologic data, environmental data, subjective data collected by an input device, and existing data about the individual from an external data source.

15. The method of claim 14, wherein the subjective data is one or more of mood or focus.

16. The method of claim 11, wherein the sleep recommendations are output via an online dashboard, via email or texts, or via verbal interfaces.

17. The method of claim 11, wherein the server further outputs optimal environmental conditions for sleep.

18. The method of claim 11, wherein the sleep data is collected using a Likert scale.

19. The method of claim 11, wherein the sleep parameters comprise sleep continuity data.

20. The method of claim 11, wherein the DVs are measured at predetermined intervals.

* * * * *